US012569015B2

(12) United States Patent (10) Patent No.: US 12,569,015 B2
Chung et al. (45) Date of Patent: *Mar. 10, 2026

(54) FUNCTIONAL FABRIC

(71) Applicant: KOLON INDUSTRIES, INC., Seoul (KR)

(72) Inventors: Il Chung, Seoul (KR); Young Soo Lee, Seoul (KR); Seong-Young Kim, Seoul (KR); Jung Eun Park, Seoul (KR)

(73) Assignee: KOLON INDUSTRIES, INC., Seoul (KR)

( * ) Notice: Subject to any disclaimer, the term of this patent is extended or adjusted under 35 U.S.C. 154(b) by 382 days.

This patent is subject to a terminal disclaimer.

(21) Appl. No.: 18/251,044

(22) PCT Filed: Oct. 28, 2021

(86) PCT No.: PCT/KR2021/015309
§ 371 (c)(1),
(2) Date: Apr. 28, 2023

(87) PCT Pub. No.: WO2022/092854
PCT Pub. Date: May 5, 2022

(65) Prior Publication Data
US 2023/0371626 A1 Nov. 23, 2023

(30) Foreign Application Priority Data

Oct. 29, 2020 (KR) ........................ 10-2020-0142417

(51) Int. Cl.
*A41D 13/11* (2006.01)
*A41D 13/005* (2006.01)
(Continued)

(52) U.S. Cl.
CPC ...... *A41D 13/1192* (2013.01); *A41D 13/0053* (2013.01); *A61F 7/02* (2013.01);
(Continued)

(58) Field of Classification Search
None
See application file for complete search history.

(56) References Cited

U.S. PATENT DOCUMENTS

2013/0239283 A1* 9/2013 Yokoyama ............... D04H 3/16
2/9
2022/0380948 A1* 12/2022 Kim ........................ D01D 5/098
(Continued)

FOREIGN PATENT DOCUMENTS

CN 1602372 A 3/2005
CN 101144217 A 3/2008
(Continued)

OTHER PUBLICATIONS

TW Office Action dated Jan. 6, 2023.

*Primary Examiner* — Arti Singh-Pandey
(74) *Attorney, Agent, or Firm* — Harvest IP Law, LLP

(57) ABSTRACT

The present invention relates to a functional fabric. More specifically, the present invention relates to a functional fabric, which causes no skin irritation, has excellent washing durability and antibacterial and deodorizing properties, quickly discharges moisture generated from the human body, such as sweat or breath, and quickly diffuses heat.

12 Claims, 3 Drawing Sheets

(51) Int. Cl.

| | |
|---|---|
| *A61F 7/00* | (2006.01) |
| *A61F 7/02* | (2006.01) |
| *A62B 18/02* | (2006.01) |
| *D02G 3/02* | (2006.01) |
| *D02G 3/44* | (2006.01) |
| *D04B 1/16* | (2006.01) |
| *D04B 1/22* | (2006.01) |
| *D04B 1/24* | (2006.01) |
| *D04B 21/16* | (2006.01) |
| *D04B 21/20* | (2006.01) |

(52) U.S. Cl.
CPC ................ *D02G 3/02* (2013.01); *D02G 3/44* (2013.01); *D04B 1/16* (2013.01); *D04B 1/22* (2013.01); *D04B 1/24* (2013.01); *D04B 21/16* (2013.01); *D04B 21/20* (2013.01); *D04B 21/207* (2013.01); *A41D 2500/10* (2013.01); *A61F 2007/0003* (2013.01); *A62B 18/02* (2013.01); *D10B 2321/021* (2013.01); *D10B 2401/021* (2013.01); *D10B 2401/04* (2013.01); *D10B 2401/063* (2013.01); *D10B 2401/13* (2013.01); *D10B 2501/00* (2013.01); *D10B 2501/042* (2013.01); *D10B 2505/04* (2013.01)

(56) References Cited

U.S. PATENT DOCUMENTS

| | | | | |
|---|---|---|---|---|
| 2023/0322979 A1* | 10/2023 | Lee | ...................... | C08F 110/02 |
| | | | | 526/352 |
| 2023/0392296 A1* | 12/2023 | Lee | ........................... | D01F 6/04 |
| 2025/0034760 A1* | 1/2025 | Lee | ...................... | D03D 15/283 |

FOREIGN PATENT DOCUMENTS

| | | | |
|---|---|---|---|
| CN | 101952363 | A | 1/2011 |
| CN | 103221600 | A | 7/2013 |
| JP | 2015071840 | A | 4/2015 |
| JP | 2015-203159 | A | 11/2015 |
| KR | 2011-0089404 | A | 8/2011 |
| KR | 20190000540 | A | 1/2019 |
| KR | 2019-0012828 | A | 2/2019 |
| KR | 20200002119 | A | 1/2020 |
| KR | 20200036171 | A | 4/2020 |
| KR | 20200043089 | A | 4/2020 |
| TW | 200712282 | A | 4/2007 |
| TW | M328457 | U | 3/2008 |

* cited by examiner

[FIG. 1]
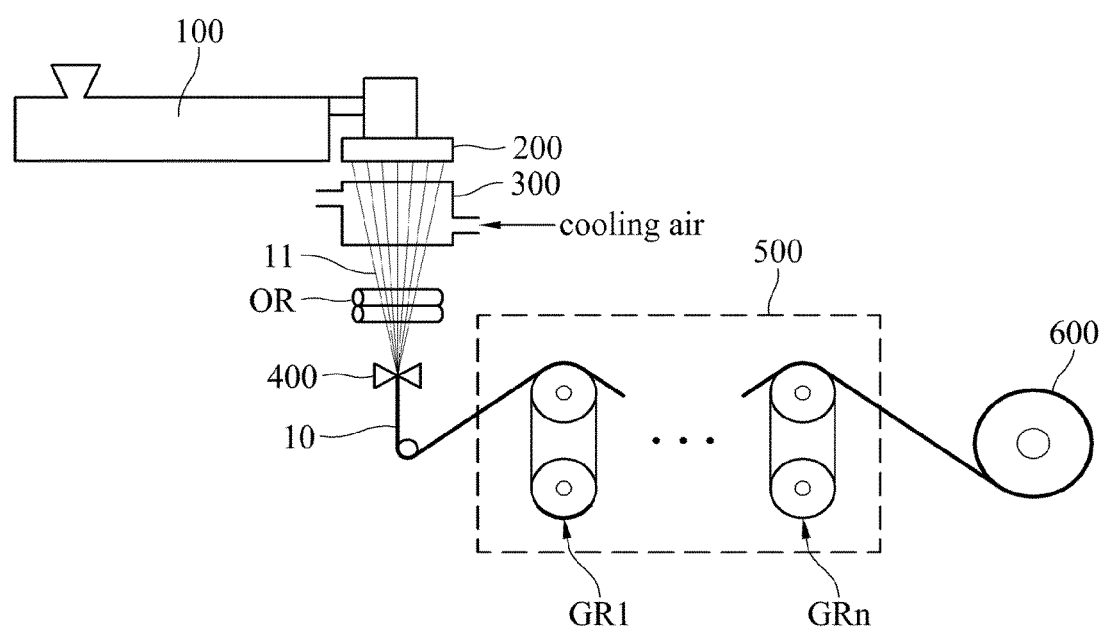

[FIG. 2]
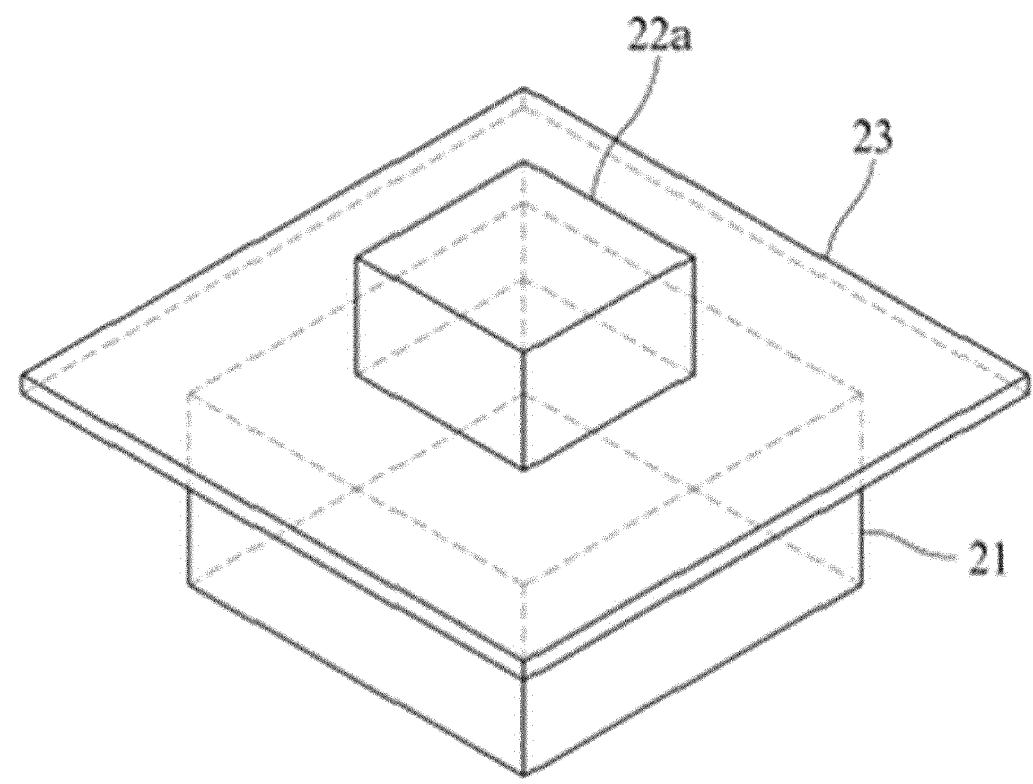

[FIG. 3]
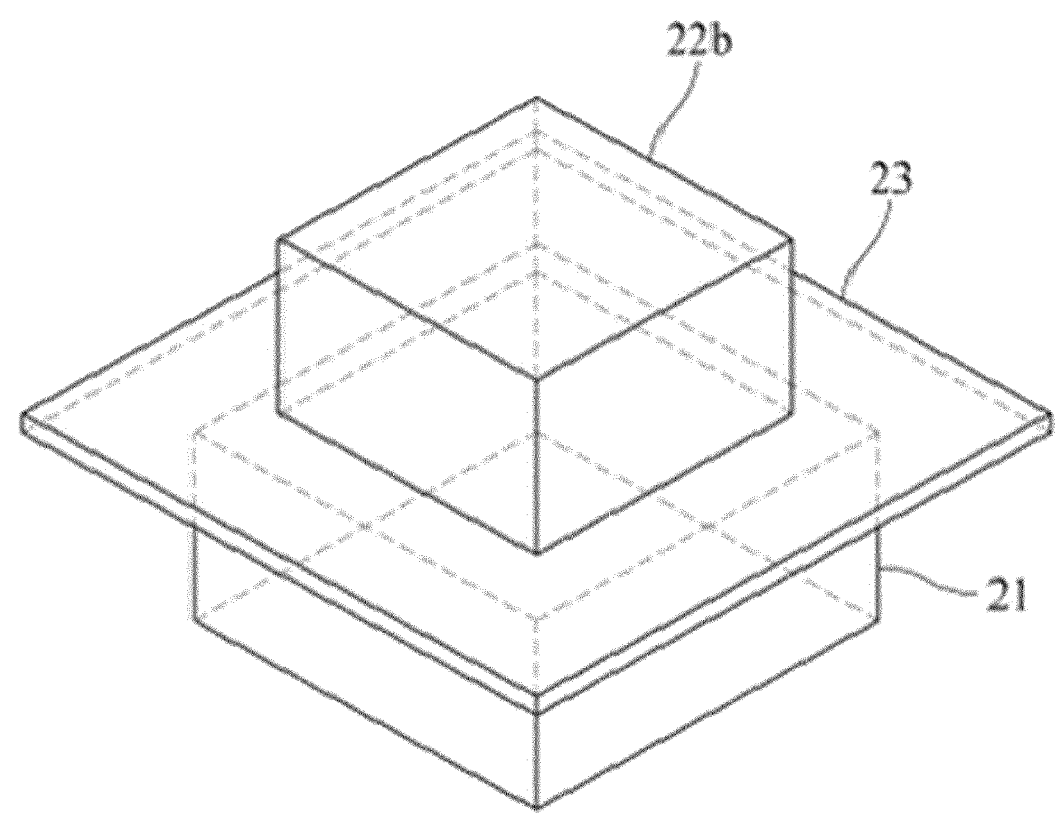

FUNCTIONAL FABRIC

CROSS REFERENCE TO RELATED APPLICATION(S)

This application is a National Stage of International Application No. PCT/KR2021/015309 filed Oct. 28, 2021, claiming priority based on Korean Patent Application No. 10-2020-0142417 filed Oct. 29, 2020, the disclosures of which are incorporated herein by reference in their entireties.

TECHNICAL FIELD

The present invention relates to a functional fabric. More particularly, the present invention relates to a functional fabric, which causes no skin irritation, has excellent washing durability, has excellent antibacterial and deodorization properties, rapidly releases moisture generated from the human body, such as sweat or breath, and rapidly diffuses heat.

BACKGROUND ART

In recent years, the use of masks is rapidly increasing due to covid-19, and side effects from the use of masks are occurring.

As the masks are worn for a long time, there are problems that masks get wet by breathing, people feel hot and stuffy since moisture and heat are not discharged well, and skin problems due to skin contact occur.

A cotton mask absorbs moisture and sweat well, but has a poor function to release them, and retains moisture all the time by breathing during the use, thereby providing a good inhabitation environment for bacteria. In addition, when the mask is exposed to moisture or sweat, mechanical properties of the fabric may rapidly deteriorate to cause a problem in durability. In addition, when the cotton mask is washed, cotton fibers formed of short fibers fall off or are exposed so that they are present in the fabric in the form of nap, thereby forming an air layer to express a heat retention effect. In addition, due to the surface roughness unique to the cotton fabric, irritation may occur upon skin contact.

In addition, masks made of a non-woven made of fabric synthetic fiber such as polyester or nylon are being used, but since the non-woven fabric is formed of short fibers, the mask irritates the skin to cause a tingling feeling when worn. In addition, when the mask is washed, the functionality of the mask is deteriorated, and short fibers fall off or partly come out of an aggregate and are present in the form of nap, thereby giving a heat retention effect. Therefore, it is impossible to wash the mask or the functionality of the mask is greatly deteriorated after washing, and when the mask is used in summer, it rather traps heat, so that one feels hot and sweaty and the skin is irritated to cause skin problems, and thus, the mask is used once and then discarded.

In addition, when a functional additive is applied on or added to the fabric for antibacterial and deodorization properties and relieving skin problems, the functionality may be temporarily imparted, but the function of the additive is deteriorated or is lost after a long term use or washing, so that it is difficult to maintain the function. In addition, the weight of the fabric is increased by the addition of the functional additive.

Accordingly, a functional fabric, which is a textile for being applied to masks, does not cause skin problems even when being directly in contact with the skin, rapidly releases breath or heat from breathing so that users do not feel uncomfortable, and has excellent antibacterial and deodorization properties without using an additional additive for imparting antibacterial and deodorization properties, is needed.

DISCLOSURE

Technical Problem

An object of the present invention for solving the problems of the prior art is to provide a functional fabric which is light to wear, may provide a soft texture when being in contact with skin in a dry state, may quickly discharge moisture generated by sweating or breathing from a human body, and may quickly diffuse and discharge heat.

Another object of the present invention is to provide a functional fabric which has a smooth surface, is formed of long fibers to have no skin irritation even in the case of being in direct contact with the human body, and has excellent antibacterial and deodorization properties in itself without an additional additive.

Another object of the present invention is to provide a functional fabric which is more flexible and has a soft texture because the functional fabric is formed of a knitted fabric.

Another object of the present invention is to provide a functional fabric which has excellent durability, may maintain a functionality even after being used for a long time and washed, and may solve the problem of not being able to be reused due to a heat-retention effect after being washed, caused in the related art, because a nap is not generated.

Still another object of the present invention is to provide a functional fabric which exhibits a functionality itself without application or impregnation of a fabric or a fiber with an additional functional additive in order to impart the functionality described above.

Technical Solution

As a result of studies conducted by the present inventors to achieve the objects, the present inventors found that all the objects may be achieved by providing a knitted fabric manufactured by using a polyethylene yarn of which a melt index, a polydispersity index, and a degree of crystallinity are within specific ranges, thereby completing the present invention. Specifically, the present inventors found that the fabric may quickly discharge moisture generated by sweating or breathing from a human body, may quickly diffuse and discharge heat to remove wetness and hotness caused by the moisture, may have a soft texture when being in direct contact with skin, may not cause skin troubles, may have excellent durability, and may maintain a functionality for a long time even after being washed, thereby completing the present invention.

In one general aspect, a functional fabric includes a knitted fabric using a polyethylene yarn which has a melt index (MI) of 0.1 to 5 g/10 min as measured at 190° C. and 2.16 kg, a polydispersity index of more than 5 and 12 or less, and a degree of crystallinity of 60 to 90%, wherein the fabric has a water contact angle of 110° or more, a surface density of 100 to 800 g/m², and a peeling resistance of grade 4 or higher as measured at a number of revolutions of 14,400 in accordance with a peeling box method specified in KS K ISO 12945-1:2014.

In an exemplary embodiment, the fabric may have a heat retention rate in accordance with KS K 0560:2018, method B of 30% or less.

In an exemplary embodiment, the fabric may have an antibacterial activity in accordance with KS K 0693:2016 of 50% or more and an ammonia deodorization rate of 10 to 30% as measured for 30 minutes to 120 minutes by a gas detection tube method.

In an exemplary embodiment, the fabric may have an abrasion resistance of 20,000 cycles or more as measured in accordance with a Martindale method specified in KS K ISO 12947-2:2014.

In an exemplary embodiment, the fabric may have a contact cooling sensation of 0.2 W/cm$^2$ or more as measured at 20±2° C. and 65±2% R.H and a thermal conductivity in the thickness direction at 20° C. of 0.1 W/mK or more.

In an exemplary embodiment, the polyethylene yarn may have a density of 0.941 to 0.965 g/cm$^3$ and weight average molecular weight of 90,000 to 400,000 g/mol.

In an exemplary embodiment, the polyethylene yarn may have an initial modulus in accordance with ASTM D2256 of 100 to 300 g/d and an elongation of 6 to 12%.

In an exemplary embodiment, the polyethylene yarn may have a tensile strength of 10 to 20 g/d.

In an exemplary embodiment, the polyethylene yarn may have a circular cross section.

In an exemplary embodiment, the polyethylene yarn may include 25 to 500 filaments, each having a fineness of 1 to 3 denier, and have a total fineness of 50 to 500 denier.

In an exemplary embodiment, the fabric may have a water contact angle of 110° or more.

In an exemplary embodiment, the fabric may have a peeling resistance of grade 4 or higher, as measured at a number of revolutions of 14,400 in accordance with a peeling box method specified in KS K ISO 12945-1:2014, after performing a washing and drying process 100 times in a washing machine standard course.

In another general aspect, a cooling mask includes the functional fabric according to the exemplary embodiment.

Advantageous Effects

The functional fabric according to the present invention may have low friction even when being in direct contact with skin, may not cause skin irritation, and may reduce wetness and hotness because the functional fabric may quickly discharge moisture generated by sweating or breathing and may dissipate heat outside.

In addition, since the durability is excellent, the pilling to be generated is small, and the abrasion resistance is significantly excellent, the nap may not be generated even after being washed, the damage of the fabric may be small even after being washed, and the period of use of the product may be extended.

In addition, the functional fabric is formed of a hydrophobic material having an official moisture regain of 0% so that it has water repellency, is rapidly dried, and decreases an inhabitation environment for bacteria to have excellent antibacterial and deodorization properties.

In addition, the functional fabric is knitted with long fibers having a high degree of crystallinity to provide a fabric which is flexible and may have a soft texture, and is light to wear so that it has an excellent wearing comfort.

The functional fabric according to the present invention may be appropriately applied to a facial mask, without limitation, and additionally, may be appropriately applied to a summer fabric. Specifically, for example, the functional fabric may be applied to a use in direct contact with the skin in summer, such as bedclothes, clothing, oversleeves, gloves, and covers.

DESCRIPTION OF DRAWINGS

FIG. 1 is a view schematically illustrating a polyethylene yarn manufacturing apparatus according to an exemplary embodiment of the present invention.

FIG. 2 is a view schematically illustrating an apparatus for measuring contact cooling sensation of a fabric.

FIG. 3 is a view schematically illustrating an apparatus for measuring a thermal conductivity in the thickness direction of a fabric.

BEST MODE

Hereinafter, the present invention will be described in more detail.

Unless otherwise defined, all technical terms and scientific terms have the same meanings as those commonly understood by one of those skilled in the art to which the present invention pertains. The terms used herein are only for effectively describing a certain specific example, and are not intended to limit the present invention.

In addition, the singular form used in the specification and claims appended thereto may be intended to also include a plural form, unless otherwise indicated in the context.

In addition, unless explicitly described to the contrary, a part "comprising" a constituent element will be understood to imply further inclusion of other constituent elements rather than the exclusion of any other constituent elements. [Polyethylene Yarn]

In an exemplary embodiment, a polyethylene yarn may have a melt index (MI) of 0.1 to 5 g/10 min as measured at 190° C. and 2.16 kg, a polydispersity index of more than 5 and 12 or less, and a degree of crystallinity of 60 to 90%, and may provide a fabric having excellent washing durability, which is light even when manufactured to have a high surface density in a range of 100 to 800 g/m$^2$ so as to more rapidly discharge moisture generated by sweating or breathing and heat within a range satisfying all of the physical properties, it is possible to provide a fabric having excellent washing durability that may be light, may have excellent durability, may not cause pilling even when being used for a long time and washed, and may maintain a functionality for a long time.

In an exemplary embodiment, the polyethylene yarn may have a melt index (MI) of 0.1 to 5 g/10 min, preferably 0.3 to 3 g/10 min, and more preferably 1 to 3 g/10 min, as measured at 190° C. and 2.16 kg. In addition, its weight average molecular weight may be 90,000 to 400,000 g/mol, preferably 100,000 to 400,000 g/mol, and more preferably 300,000 to 350,000 g/mol. Within the range, the melt flowability during the melt extrusion of yarn is preferable, occurrence of thermal decomposition is prevented, and processability such as no breakage during drawing is secured, thereby manufacturing a yarn having uniform physical properties, and a fabric having excellent durability and washing durability may be provided. Specifically, a fabric which has a peeling resistance of grade 4 or higher, more preferably grade 4 or 5, as measured at a number of revolutions of 14,400 in accordance with the peeling box method specified in KS K ISO 12945-1:2014 may be provided. In addition, a fabric having a peeling resistance of grade 4 or higher, more preferably grade 5 even after washing 100 times or more may be provided. In addition, a fabric which has an abrasion resistance of 20,000 cycles or more as measured in accordance with a Martindale method specified in KS K ISO 12947-2:2014 may be provided.

Within a range where the peeling resistance and the abrasion resistance satisfy the above range, occurrence of skin problems when applying the yarn to a fabric in direct contact with the skin such as masks may be prevented, and a nap generated by peeling is prevented to prevent occurrence of hotness. More specifically, a fabric having a heat retention rate in accordance with KS K 0560:2018, method B of 30% or less, preferably 5 to 30% may be provided.

In addition, by using a high-density polyethylene (HDPE) satisfying a density of 0.941 to 0.965 g/cm³ and a polydispersity index of more than 5 and 12 or less, more preferably more than 5 and 9 or less, a fiber having a degree of crystallinity of 60 to 90% may be obtained by melt spinning. The degree of crystallinity of the polyethylene yarn may be derived together with a micro-crystallite size at the time of crystallinity analysis using an X-ray diffraction analyzer. Within a range where the degree of crystallinity satisfies the above range, heat rapidly diffuses and dissipates through lattice vibration called a "phonon" in a direction of a molecular chain connected by a covalent bond of high-density polyethylene (HDPE), and a function to discharge moisture generated by sweating or breathing from a human body is improved, thereby providing a fabric having an excellent wearing feeling. More specifically, a fabric which has a contact cooling sensation of 0.2 W/cm² or more as measured at 20±2° C. and 65±2% R.H and a thermal conductivity in the thickness direction at 20° C. of 0.1 W/mK or more may be provided. More specifically, the fabric may have a contact cooling sensation of 0.2 to 0.8 W/cm² or more as measured at 20±2° C. and 65±2% R.H and a thermal conductivity in the thickness direction at 20° C. of 0.1 to 0.3 W/mK.

Since the polyethylene yarn may be melt spun, the fabric satisfies the physical properties of a substantially low official moisture regain of 0%, excellent water repellency, and a water contact angle of 110° C. or more, more preferably 110 to 150°, so that the fabric immediately releases moisture without retaining it when being in direct contact with the skin, and thus, may minimize a inhabitation environment for bacteria and the like and has antibacterial and deodorization properties in itself without an additional additive. Specifically, a fabric which has an antibacterial activity in accordance with KS K 0693:2016 of 50% or more, specifically 50 to 90%, and an ammonia deodorization rate of 10 to 30% as measured for 30 minutes to 120 minutes by a gas detection tube method may be provided.

In an exemplary embodiment, the fabric may have an initial modulus in accordance with ASTM D2256 of 100 to 300 g/d, preferably 120 to 200 g/d, an elongation of 6 to 12%, preferably 8 to 12%, and a tensile strength of 10 to 20 g/d, preferably 12 to 20 g/d. Though it is not limited thereto, the fabric may be more flexible, impart more elasticity and flexibility after being knitted, and provide an excellent wearing comfort by satisfying the range. In addition, within the range, occurrence of peeling caused by fraction may be minimized and damage to a fabric due to friction may be prevented, and thus, it is more preferred.

In an exemplary embodiment, it is preferred that the yarn may have a circular cross section shape, but is not limited thereto. By manufacturing the fabric to have a circular cross section, adsorption of moisture on a fiber surface is minimized and the moisture may be immediately discharged, thereby providing a fabric having better antibacterial and deodorization properties.

In an exemplary embodiment, the yarn may include 25 to 500 filaments, each having a fineness of 1 to 3 denier, and have a total fineness of 50 to 500 denier. Within the range, a fabric which is light and has excellent durability and washing durability may be provided.

Hereinafter, a method for manufacturing a polyethylene yarn according to an exemplary embodiment of the present invention will be described in detail, with reference to FIG. 1. The method for manufacturing a polyethylene yarn of the present invention is not limited as long as the polyethylene yarn satisfies the range of the physical properties such as water contact angle, surface density, and peeling resistance, and an embodiment is described in the following.

First, polyethylene in the form of chips is introduced into an extruder 100 and melted to obtain a polyethylene melt.

The molten polyethylene is transported through a spinneret 200 by a screw (not illustrated) in the extruder 100, and extruded through a plurality of holes formed in the spinneret 200. The number of holes of the spinneret 200 may be determined by the denier per filament (DPF) and the fineness of the yarn to be manufactured. For example, when a yarn having a total fineness of 75 denier is manufactured, the spinneret 200 may have 20 to 75 holes, and when a yarn having a total fineness of 450 denier is manufactured, the spinneret 200 may have 90 to 450, preferably 100 to 400 holes.

A melting process in the extruder 100 and an extrusion process through the spinneret 200 may be changed and applied depending on the melt index of the polyethylene chips, but specifically, for example, may be performed at 150 to 315° C., preferably 250 to 315° C., and more preferably 265 to 310° C. That is, the extruder 100 and the spinneret 200 may be maintained at 150 to 315° C., preferably 250 to 315° C., and more preferably 265 to 310° C.

When the spinning temperature is lower than 150° C., polyethylene does not melt uniformly due to the low spinning temperature, so that the spinning may be difficult. However, when the spinning temperature is higher than 315° C., thermal decomposition of polyethylene is caused, so that a desired strength may not be expressed.

A ratio (L/D) of a hole length (L) to a hole diameter (D) of the spinneret 200 may be 3 to 40. When L/D is less than 3, die swelling occurs during melt extrusion and it becomes hard to control the elastic behavior of polyethylene to deteriorate spinnability, and when L/D is more than 40, a yarn breakage may occur due to a necking phenomenon of the molten polyethylene passing through the die 200, and discharge unevenness may occur due to a decrease in pressure.

As the molten polyethylene is discharged from the holes of the spinneret 200, solidification of polyethylene starts due to a difference between a spinning temperature and room temperature to form filaments 11 in a semi-solidified state. In the present specification, not only the filaments in a semi-solidified state but also completely solidified filaments are collectively referred to as "filaments".

A plurality of filaments 11 are cooled in a cooling section (or "quenching zone") 300 so that they are completely solidified. The filaments 11 may be cooled in a manner of air cooling.

It is preferred that the cooling of the filaments 11 in the cooling section 300 may be performed so that the filaments are cooled to 15 to 40° C., using a cooling air at a wind speed of 0.2 to 1 m/sec. When the cooling temperature is lower than 15° C., elongation is insufficient due to supercooling, so that breakage may occur in a drawing process, and when the cooling temperature is higher than 40° C., a deviation in fineness between the filaments 11 is increased due to non-uniformity of solidification, which may cause a yarn breakage during the drawing process.

In addition, multi-stage cooling is performed during cooling in the cooling section so that more uniform crystallization may be obtained, and thus, a yarn which may discharge moisture and sweat more smoothly and has excellent anti-bacterial and deodorization properties may be manufactured. More specifically, the cooling section may be divided into three or more sections. For example, when the cooling section includes three cooling sections, it is preferred to design the cooling section so that the temperature is gradually lowered from a first cooling section to a third cooling section. Specifically, for example, the first cooling section may be set to 40 to 80° C., a second cooling section may be set to 30 to 50° C., and the third cooling section may be set to 15 to 30° C.

In addition, a wind speed is set to the highest in the first cooling section, thereby manufacturing a fiber having a smoother surface. Specifically, the first cooling section may be cooled to 40 to 80° C. using a cooling wind at a wind speed of 0.8 to 1 m/sec, the second cooling section may be set to 30 to 50° C. using a cooling wind at a wind speed of 0.4 to 0.6 m/sec, and the third cooling section may be set to 15 to 30° C. using a cooling wind at a wind speed of 0.2 to 0.5 m/sec, and by making adjustment to the conditions as such, a yarn having higher degree of crystallinity and a smoother surface may be manufactured.

Subsequently, the cooled and completely solidified filaments 11 are collected by an interlacer 400 to form a multi-filament 10.

As illustrated in FIG. 1, the polyethylene yarn of the present invention may be manufactured by a direct spinning drawing (DSD) process. That is, the multi-filament 10 may be directly transported to a multi-stage drawing unit 500 including a plurality of godet roller parts ($GR_1$, . . . $Gr_n$), drawn in multiple stages at a total drawing ratio of 2 to 20 times, preferably 3 to 15 times, and then wound up on a winder 600. In addition, in the last drawing section in the multi-stage drawing, shrinkage drawing (relaxation) at 1 to 5% may be applied to provide a yarn having better durability.

Alternatively, the polyethylene yarn of the present invention may be manufactured by winding the multi-filament 10 as an undrawn yarn and then drawing the undrawn yarn. That is, the polyethylene yarn of the present invention may be manufactured through a two-stage process of melt-spinning polyethylene to manufacture an undrawn yarn and then drawing the undrawn yarn.

When the total drawing ratio applied in the drawing process is less than 2, the polyethylene yarn finally obtained may not have a degree of crystallinity of 60% or more, and there is a risk of causing lint (peeling) on the fabric manufactured by the yarn.

However, when the total draw ratio is more than 15, breakage may occur, the strength of the finally obtained polyethylene yarn is not appropriate, so that the weavability of the polyethylene yarn may not be good, and the fabric manufactured using the yarn is too stiff, so that a user may feel uncomfortable.

When a linear speed of the first godet roller part ($GR_1$) which determines the spinning speed of the melt spinning of the present invention is determined, the linear speeds of the remaining godet roller parts are appropriately determined so that a total drawing ratio of 2 to 20, preferably 3 to 15 may be applied to the multi-filament 10 in the multi-stage drawing unit 500.

According to an exemplary embodiment of the present invention, the temperature of the godet roller parts ($GR_1$, . . . $Gr_n$) in the multi-stage drawing unit 500 is appropriately set in a range of 40 to 140° C., thereby performing heat setting of the polyethylene yarn by the multi-stage drawing unit 500. Specifically, for example, the multi-stage drawing unit may include 3 or more, specifically 3 to 5 drawing sections. In addition, each drawing section may be composed of a plurality godet roller parts.

Specifically, for example, the multi-stage drawing unit may be composed of 4 drawing sections, and the drawing may be performed at a total drawing ratio of 7 to 15 times in a first drawing section to a third drawing section, and then a shrinkage drawing (relaxation) at 1 to 3% may be performed in a fourth drawing section. The total drawing ratio refers to a final drawing ratio of a fiber which passes through the first drawing section to the third drawing section, as compared with a fiber before drawing.

More specifically, the first drawing section may be performed at 40 to 130° C. and a total drawing ratio may be 2 to 5 times. The second drawing section may be performed at a higher temperature than the first drawing section, specifically at 100 to 150° C., and drawing may be performed so that the total drawing ratio is 5 to 8 times. The third drawing section may be performed at 100 to 150° C., and drawing may be performed so that the total drawing ratio is 7 to 15 times. The fourth drawing section may be performed at a temperature equivalent to or higher than the second drawing section, specifically at 80 to 140° C., and shrinkage drawing (relaxation) at 1 to 3% may be performed.

Both the multi-stage drawing and the heat-setting of the multi-filament 10 are performed simultaneously by the multi-stage drawing unit 500, and the drawn multi-filament 10 in multiple stages is wound up on a winder 600, thereby completing the polyethylene yarn of the present invention.

[Functional Fabric]

In an exemplary embodiment, the functional fabric may include the polyethylene yarn described above alone and may further include a heterogeneous yarn for further imparting other functionalities, but it is preferred to use only the polyethylene yarn from the point of view of water repellency and prevention of a heating sensation.

In addition, in an exemplary embodiment of the present invention, it is more preferred that the functional fabric is knitted, since it has excellent flexibility, may provide a light fabric as compared with a textile even with an increased surface density, and when applied to a mask, may prevent occurrence of skin problems even in the case of being in contact with the skin for a long time. In a case of a woven fabric or a non-woven fabric, a nap may be generated or short fibers may come out after being washed, which may cause skin irritation. Therefore, it is preferable that a knitted fabric is used in the present invention.

The functional fabric according to an exemplary embodiment of the present invention may satisfy all of the physical properties of a water contact angle of 110° or more, preferably 130° or more, and specifically 110 to 150°, a surface density of 100 to 800 $g/m^2$ and preferably 150 to 800 $g/m^2$ and a peeling resistance of grade 4 or higher and preferably grade 4 or 5, as measured at a number of revolutions of 14,400 in accordance with a peeling box method specified in KS K ISO 12945-1:2014, and within the range, it was confirmed that the functional fabric may rapidly discharge moisture generated by sweating or breathing and heat and maintain the function even after prolonged washing.

In addition, the functional fabric may satisfy all of the physical properties of a heat retention rate in accordance with KS K 0560:2018, method B of 30% or less, preferably 27% or less, an antibacterial activity in accordance with KS K 0693:2016 of 50% or more, preferably 50 to 70% without an additional antibacterial agent, an ammonia deodorization rate of 10 to 30% as measured for 30 minutes to 120 minutes by a gas detection tube method, an abrasion resistance of 20,000 cycles or more as measured in accordance with a Martindale method specified in KS K ISO 12947-2:2014, a contact cooling sensation of 0.2 $W/cm^2$ or more as measured at 20±2° C. and 65±2% R.H, and a thermal conductivity in the thickness direction at 20° C. of 0.1 W/mK or more. The physical properties to be desired may be all achieved in the above ranges, which are thus preferred.

In addition, the functional fabric according to an exemplary embodiment of the present invention may maintain the retention rate of the physical properties of 70% or more, 80% or more, and more preferably 90% or more even after being washed 100 times.

Hereinafter, the present invention will be described in more detail with reference to the examples and the comparative examples. However, the following examples and comparative examples are only an example for describing the present invention in more detail, and do not limit the present invention in any way.

The physical properties were measured as follows.

<Weight Average Molecular Weight (Mw) (g/Mol) and Polydispersity Index (PDI)>

A polyethylene yarn was completely dissolved in the following solvent and then each of the weight average molecular weight (Mw) and the polydispersity index (Mw/Mn: PDI) of the polyethylene yarn was determined, using the following gel permeation chromatography (GPC).

Analytical instrument: HLC-8321 GPC/HT available from Tosoh Corporation

Column: PLgel guard (7.5×50 mm)+2×PLgel mixed-B (7.5×300 mm)

Column temperature: 160° C.

Solvent: trichlorobenzene (TCB)+0.04 wt % of dibutylhydroxytoluene (BHT) (after drying with 0.1% $CaCl_2$))

Injector, Detector temperature: 160° C.

Detector: RI Detector

Flow velocity: 1.0 ml/min

Injection amount: 300 µl

Sample concentration: 1.5 mg/mL

Standard sample: polystyrene

<Tensile Strength (g/d), Initial Modulus (g/d), and Elongation (%)>

According to the method of ASTM D2256, a universal tensile tester available from Instron (Instron Engineering Corp, Canton, Mass) was used to obtain a strain-stress curve of the polyethylene yarn. A sample length was 250 mm, a tensile speed was 300 mm/min, and an initial load was set to 0.05 g/d. The tensile strength (g/d) and the elongation (%) were obtained from the stress and the stretch at break, and the initial modulus (g/d) was determined from a tangent which imparts a maximum gradient near the starting point of the curve. The measurement was performed five times for each yarn and the average value was calculated.

<Degree of Crystallinity of Yarn>

An XRD instrument (X-ray Diffractometer) [manufacturer: PANalytical, model name: EMPYREAN] was used to measure the degree of crystallinity of the polyethylene yarn. Specifically, the polyethylene yarn was cut to prepare a sample having a length of 2.5 cm, the sample was fixed to a sample holder, and the measurement was performed under the following conditions:

10

Light source (X-ray Source): Cu-Kα radiation

Power: 45 KV×25 mA

Mode: continuous scan mode

Scan angle range: 10 to 40°

Scan speed: 0.1°/sec

<Melt Index>

Measurement was performed at 190° C. and 2.16 kg in accordance with ASTM D 1238.

<Water Contact Angle>

A dynamic water contact angle tester (manufactured by Fibro, 1100DAT) was used to add 4 µl of distilled water dropwise to the surface of a sheet, and a water contact angle 30 seconds after the addition was measured.

<Peeling Resistance>

A Martindale tester was used to measure the peeling resistance of a fabric at a number of revolutions of 14,400 in accordance with the peeling box method specified in KS K ISO 12945-1:2014. The peeling resistance rating criteria were as follows:

Grade 1: very severe peeling

Grade 2: severe peeling

Grade 3: medium peeling

Grade 4: slight peeling

Grade 5: no peeling

<Durability after Washing>

The manufactured fabric was subjected to a washing and drying process 100 times in a washing machine standard course, and then the physical properties were compared with those of the initial fabric before washing.

1) Peeling Resistance after Washing

The peeling resistance test was performed after being washed 100 times.

2) Heat Retention Change after Washing

The heat retention test was performed after washing 100 times.

3) Skin Irritation after Washing

The skin irritation test was performed after being washed 100 times.

4) Antibacterial Property Changes after Washing

The antibacterial property test was performed after being washed 100 times.

<Heat Retention Rate>

A heat retention rate was measured in accordance with method B of KS K 0560:2018 B, which was commissioned to the Korea Apparel Testing & Research Institute.

<Antibacterial Activity>

An antibacterial activity (%) was measured in accordance with KS K 0693:2016, which was commissioned to the Korea Apparel Testing & Research Institute.

Species tested: *Staphylococcus aureus* ATCC 6538

*Klebsiella pneumoniae* ATCC 4352

Concentration of inoculum solution: $1.1×10^5$ CFU/mL of *Staphylococcus aureus*

$0.8×10^5$ CFU/mL of *Klebsiella pneumoniae*

Control: standard cotton cloth

Non-ionic surfactant: Tween 80, added 0.05% of inoculum solution

<Deodorization Property>

An ammonia deodorization rate was evaluated by the gas detection tube method, which was commissioned to the Korea Apparel Testing & Research Institute.

Test period: 30 minutes, 60 minutes, 90 minutes, and 120 minutes

<Test Conditions>

Amount of sample: 10 cm×10 cm (2.0 g)

Gas tested: ammonia

Concentration of injected gas tested: 500 µg/mL

Volume of container: 1000 mL

Test environment: temperature: 20° C., humidity: 65%

Deodorization rate (%)=[(concentration of blank
gas−concentration of sample gas)/(concentration
of blank gas]×100

<Skin Irritation>

A mask was manufactured using the fabric and then was worn for 8 hours by 30 men and women in their teens and twenties, and skin irritation was visually determined.

Pimple occurrence, redness, and stinging degrees were rated on a 5-point scale, and the average values were determined.

This means that pimple occurrence, redness, and stinging get worse from 1 to 5.

<Contact Cooling Sensation>

A KES-F7 (Thermo Labo II) was used to perform the measurement in a test environment of 20±2° C. and 65±2% R.H, which was commissioned to the Korea Apparel Testing & Research Institute.

Specifically, a fabric sample having a size of 20 cm×20 cm was prepared, and was allowed to stand for 24 hours under the conditions of a temperature of 20±2° C. and 65±2% RH. Subsequently, a KES-F7 THERMO LABO II device (Kato Tech Co. LTD.) was used to measure a contact cooling sensation (Q max) of the fabric under the test environments of a temperature of 20±2° C. and 65±2% RH. Specifically, as illustrated in FIG. 2, the fabric sample 23 was placed on a base plate (also referred to as "Water-Box") 21 maintained at 20° C., and a T-Box 22a heated to 30° C. (contact area: 3 cm×3 cm) was placed on the fabric sample 23 only for 1 second. That is, the other surface of the fabric sample 23 of which one surface was in contact with the base place 21 was momentarily brought into contact with T-Box 22a. A contact pressure applied to the fabric sample 23 by the T-Box 22a was 6 gf/cm². Subsequently, a Q max value displayed on a monitor (not shown) connected to the device was recorded. The test as such was repeated 10 times, and an arithmetic mean of the Q max values was calculated.

<Thermal Conductivity>

A fabric sample having a size of 20 cm×20 cm was prepared, and was allowed to stand for 24 hours under the conditions of a temperature of 20±2° C. and 65±2% RH. Subsequently, a KES-F7 THERMO LABO II device (Kato Tech Co. LTD.) was used to measure the thermal conductivity and the heat transfer coefficient of the fabric under the test environments of a temperature of 20±2° C. and 65±2% RH. Specifically, as illustrated in FIG. 3, the fabric sample 23 was placed on the base plate 21 maintained at 20° C., and a BT-Box 22b heated to 30° C. (contact area: 5 cm×5 cm) was placed on the fabric sample 23 for 1 minute. Heat was continuously supplied to the BT-Box 22b so that the temperature was maintained at 30° C. even while the BT-Box 22b was in contact with the fabric sample 23. A heat quantity supplied for temperature maintenance of the BT-Box 22b (that is, heat flow loss) was displayed on a monitor (not shown) connected to the device. The test was repeated 5 times, and the arithmetic mean of the heat flow loss was calculated. Subsequently, the thermal conductivity and the heat transfer coefficient of the fabric were calculated using the following Equations 2 and 3:

$$K=(W \cdot D)/(A \cdot \Delta T) \qquad \text{Equation 2:}$$

$$k=K/D \qquad \text{Equation 3:}$$

wherein K is a thermal conductivity (W/cm·° C.), D is a thickness (cm) of the fabric sample 23, A is a contact area of the BT-Box 22b (=25 cm²), ΔT is a temperature difference (=10° C.) between the two surfaces of the fabric sample 23, W is a heat flow loss (Watt), and k is a heat transfer coefficient (W/cm²·° C.).

<Abrasion Resistance>

A Martindale tester was used to measure the abrasion resistance of a fabric in accordance with the Martindale method specified in KS K ISO 12947-2:2014. Specifically, the number of times (cycles) until two yarns broke in the fabric was measured.

Example 1

<Manufacture of Polyethylene Yarn>

An apparatus illustrated in FIG. 1 was used to manufacture a polyethylene yarn including 200 filaments and having a total fineness of 150 denier.

Specifically, polyethylene chips having a density of 0.960 g/cm³, a weight average molecular weight (Mw) of 328,000 g/mol, a polydispersity index (PDI) of 7.8, and a melt index (MI at 190° C.) of 1.5 g/10 min were added to an extruder 100 and were melted. The molten polyethylene was extruded through a spinneret 200 having 200 holes. L/D which is a ratio of a hole length (L) to a hole diameter (D) of the spinneret 200 was 6. A spinneret temperature was 270° C.

Filaments 11 formed by the discharge from nozzle holes of the spinneret 200 were sequentially cooled in a cooling section 300 composed of three sections. The filaments were cooled to 50° C. by a cooling wind at a wind speed of 0.9 m/sec in the first cooling section, cooled to 35° C. by a cooling wind at a wind speed of 0.5 m/sec in the second cooling section, and finally cooled to 25° C. by a cooling wind at a wind speed of 0.4 m/sec in the third cooling section. After the cooling, the filaments were collected into a multi-filament yarn 10 by an interlacer 400.

Subsequently, the multi-filament yarn was transported to a drawing part 500. The drawing part was composed of a multi-stage drawing unit composed of four sections, and specifically, the filaments were drawn to a total drawing ratio of 3 times at a highest drawing temperature of 100° C. in the first drawing section, drawn to a total drawing ratio of 8 times at a highest drawing temperature of 140° C. in the second drawing section, drawn to a total drawing ratio of 10 times at a highest drawing temperature of 130° C. in the third drawing section, and drawn and heat set so as to be shrunk and drawn (relaxed) by 2% as compared with the third drawing section at a highest drawing temperature of 120° C. in the fourth drawing section.

Subsequently, the drawn multi-filament yarn was wound up on a winder 600. A winding tension was 0.8 g/d.

The physical properties of the thus-manufactured yarn were measured, and are shown in the following Table 1.

<Manufacture of Functional Fabric>

Knitting was performed using the polyethylene yarn manufactured above to manufacture a knitted fabric. The physical properties of the knitted fabric manufactured were measured, and are shown in the following Table 3.

Examples 2 to 7

Knitted fabrics were manufactured in the same manner as in Example 1, except that the conditions were changed as shown in Table 1.

In addition, the physical properties of the fabrics manufactured in the same manner as in Example 1 were measured and are shown in the following Table 3.

Comparative Examples 1 to 3

Knitted fabrics were manufactured in the same manner as in Example 1, except that the conditions were changed as shown in Table 2.

In addition, the physical properties of the fabrics manufactured in the same manner as in Example 1 were measured and are shown in the following Table 4.

Comparative Example 4

A knitted fabric was manufactured using the same raw material as Example 1 in the same manner as in Example 1, except that the conditions of the cooling process and the drawing process were changed as follows.

During the cooling process, the filaments were finally cooled to 25° C. by a cooling wind at a wind speed of 0.5 m/sec in the cooling section 300, collected to a multi-filament 10 by an interlacer 400, and transported to a multi-stage drawing unit 500.

During the drawing process, drawing was performed in a drawing section composed of a total of one section. The drawing section was composed of a total of 5-stage godet roller parts, and the temperature of the godet roller parts was set to 80 to 125° C., but the temperature of the godet roller part at the rear end was set to be higher than the temperature of the godet roller part at the immediately previous stage. The drawing was performed at a total drawing ratio of 7.5.

The physical properties of the manufactured fabric were measured, and are shown in the following Table 4.

Comparative Example 5

A knitted fabric was manufactured using the same raw material as Example 1 in the same manner as in Example 1, except that the drawing temperatures in the first to fourth drawing sections were 140° C.

In addition, the physical properties of the fabrics manufactured in the same manner as in Example 1 were measured and are shown in the following Table 4.

Comparative Example 6

A knitted fabric was manufactured using the same raw material as Example 1 in the same manner as in Example 1, except that the drawing temperatures of the first and second drawing sections were 120° C. and the drawing temperatures of the third and fourth drawing sections were 80° C.

In addition, the physical properties of the fabrics manufactured in the same manner as in Example 1 were measured and are shown in the following Table 4.

Comparative Example 7

A knitted fabric was manufactured in the same manner as in Comparative Example 4, except that the conditions were changed as shown in the following Table 2.

In addition, the physical properties of the fabrics manufactured in the same manner as in Example 1 were measured and are shown in the following Table 4.

Comparative Example 8

A knitted fabric was manufactured in the same manner as in Example 1, except that the conditions were changed as shown in Table 2.

In addition, the physical properties of the fabrics manufactured in the same manner as in Example 1 were measured and are shown in the following Table 4.

Comparative Example 9

A knitted fabric was manufactured in the same manner as in Example 1, using a rayon yarn having a circular cross section, and then the physical properties of the fabric were evaluated. It was confirmed that the contact cooling sensation was 0.085 W/cm$^2$ which was very low and a thermal conductivity was 0.0260 W/mK which was lower than the examples. In addition, it was confirmed that skin irritation was grade 4 which was not good and the skin irritation was worse after washing.

Comparative Example 10

A knitted fabric was manufactured in the same manner as in Example 1, using a polyethylene terephthalate yarn having a circular cross section, and then the physical properties of the fabric were evaluated. It was confirmed that the contact cooling sensation was 0.119 W/cm$^2$ which was very low and a thermal conductivity was 0.1109 W/mK which was lower than the examples. In addition, it was confirmed that skin irritation was grade 3 which was not good and the skin irritation was worse after washing.

TABLE 1

| | | Example 1 | Example 2 | Example 3 | Example 4 | Example 5 | Example 6 | Example 7 |
|---|---|---|---|---|---|---|---|---|
| Physical properties of chips | Mw (g/mol) | 328,000 | 328,000 | 328,000 | 328,000 | 328,000 | 328,000 | 282,000 |
| | MI (g/10 min) | 1.5 | 1.0 | 1.0 | 0.3 | 3 | 1.5 | 0.7 |
| | PDI | 7.8 | 5.6 | 7.8 | 7.4 | 7.8 | 9.8 | 10.2 |
| | Number of cooling sections | 3 | 3 | 3 | 3 | 3 | 3 | 3 |
| | Number of drawing sections | 4 | 4 | 4 | 4 | 4 | 4 | 4 |
| | Total drawing ratio (times) | 10 | 11 | 8.5 | 10 | 10 | 10 | 10 |
| | Relaxation rate (%) | 2 | 2 | 2 | 2 | 2 | 2 | 2 |
| | Winding tension (g/d) | 0.8 | 0.8 | 0.8 | 0.8 | 0.8 | 0.8 | 0.8 |
| Physical properties of yarn | Mw (g/mol) | 312891 | 306601 | 314572 | 314265 | 316842 | 305842 | 274853 |
| | MI (g/10 min) | 1.7 | 1.2 | 1.2 | 0.4 | 3.3 | 1.6 | 0.8 |
| | PDI | 9.6 | 7.7 | 9.5 | 9.5 | 9.6 | 10.5 | 11.8 |
| | Degree of crystallinity (%) | 75.1 | 75.6 | 73.2 | 72.1 | 70.5 | 70.2 | 69.5 |

TABLE 1-continued

|  | Example 1 | Example 2 | Example 3 | Example 4 | Example 5 | Example 6 | Example 7 |
|---|---|---|---|---|---|---|---|
| Tensile strength (g/d) | 13.02 | 13.8 | 12.0 | 11.5 | 10.5 | 10.9 | 9.5 |
| Initial modulus (g/d) | 160 | 203 | 141 | 125 | 137 | 120 | 155 |
| Elongation (%) | 9.4 | 9.0 | 9.8 | 10.1 | 11.5 | 10.5 | 12.0 |

TABLE 2

|  |  | Comparative Example 1 | Comparative Example 2 | Comparative Example 3 | Comparative Example 4 | Comparative Example 5 | Comparative Example 6 | Comparative Example 7 | Comparative Example 8 |
|---|---|---|---|---|---|---|---|---|---|
| Physical properties of chips | Mw (g/mol) | 328,000 | 328,000 | 450,000 | 328,000 | 328,000 | 328,000 | 153,828 | 315,000 |
|  | MI (g/10 min) | 7 | 1.5 | 8 | 1.5 | 1.5 | 1.5 | 18 | 12 |
|  | PDI | 7.8 | 11.5 | 7.8 | 7.8 | 7.8 | 7.8 | 3.2 | 8.5 |
|  | Number of cooling sections | 3 | 3 | 3 | 1 | 3 | 3 | 1 | 3 |
|  | Number of drawing sections | 4 | 4 | 4 | 1 | 4 | 4 | 1 | 4 |
|  | Total drawing ratio (times) | 10 | 10 | 10 | 6 | 10 | 10 | 6 | 9 |
|  | Relaxation rate (%) | 2 | 2 | 2 | 0 | 2 | 2 | 2 | 2 |
|  | Winding tension (g/d) | 0.8 | 0.8 | 0.8 | 0.8 | 0.8 | 0.8 | 0.8 | 0.8 |
| Physical properties of yarn | Mw (g/mol) | 316852 | 324123 | 423573 | 306000 | 313652 | 304211 | 124,283 | 298,000 |
|  | MI (g/10 min) | 7.3 | 1.6 | 8 | 1.8 | 1.6 | 1.1 | 19 | 12.8 |
|  | PDI | 9.6 | 13.5 | 9.5 | 9.6 | 9.6 | 7.7 | 4.2 | 10.5 |
|  | Degree of crystallinity (%) | 75.1 | 75.6 | 73.2 | 58 | 64.5 | 65.7 | 63 | 72.3 |
|  | Tensile strength (g/d) | 8.7 | 8.8 | 6.7 | 5.5 | 7.2 | 7.8 | 3.1 | 6.8 |
|  | Initial modulus (g/d) | 115 | 124 | 105 | 89 | 90 | 88 | 70 | 115 |
|  | Elongation (%) | 12.0 | 12.1 | 11.8 | 13.9 | 12.8 | 13.2 | 22 | 14 |

TABLE 3

|  | Example 1 | Example 2 | Example 3 | Example 4 | Example 5 | Example 6 | Example 7 |
|---|---|---|---|---|---|---|---|
| Water contact angle (°) | 132.1 | 133.8 | 131.1 | 125 | 120.5 | 121.7 | 110.5 |
| Surface density (g/m$^2$) | 170 | 259 | 350 | 180 | 185 | 180 | 175 |
| Peeling resistance (grade) | 4-5 | 4-5 | 4-5 | 4-5 | 4 | 4 | 4 |
| Heat retention rate (%) | 21.7 | 23.3 | 26.7 | 25.8 | 28.5 | 29.7 | 27.5 |
| Antibacterial activity (%) | 56.3 | 55.8 | 50.8 | 50.5 | 50.7 | 50.2 | 42.1 |
| Skin irritation (grade) | 1 | 1 | 1 | 1 | 1 | 1 | 1 |
| Abrasion resistance (cycles) | 20,000 or more | 20,000 or more | 20,000 or more | 20,000 or more | 20,000 or more | 20,000 or more | 20,000 or more |
| Contact cooling sensation (W/cm$^2$) | 0.206 | 0.212 | 0.202 | 0.205 | 0.201 | 0.200 | 0.210 |
| Thermal conductivity in the thickness direction at 20° C. (W/mK) | 0.1681 | 0.1045 | 0.1550 | 0.1445 | 0.1124 | 0.1014 | 0.1007 |

TABLE 3-continued

|  |  | Example 1 | Example 2 | Example 3 | Example 4 | Example 5 | Example 6 | Example 7 |
|---|---|---|---|---|---|---|---|---|
| Washing | Peeling resistance (grade) | 4-5 | 4-5 | 4-5 | 4 | 3 | 3 | 2 |
|  | Heat retention rate (%) | 22.1 | 22.7 | 26.9 | 27.8 | 30.5 | 33.7 | 35.1 |
|  | Skin irritation (grade) | 1 | 1 | 1 | 1 | 2 | 2 | 2 |
|  | Antibacterial activity (%) | 55.5 | 55.2 | 49.5 | 50.1 | 42.7 | 40.1 | 35.7 |

TABLE 4

|  | Comparative Example 1 | Comparative Example 2 | Comparative Example 3 | Comparative Example 4 | Comparative Example 5 | Comparative Example 6 | Comparative Example 7 | Comparative Example 8 |
|---|---|---|---|---|---|---|---|---|
| Water contact angle (°) | 109.1 | 105.8 | 80.7 | 125 | 110.5 | 111 | 121 | 112 |
| Surface density (g/m²) | 150 | 157 | 159 | 170 | 180 | 180 | 170 | 250 |
| Peeling resistance (grade) | 3 | 3 | 2 | 3 | 3 | 2 | 3 | 2 |
| Heat retention rate (%) | 35.7 | 32.4 | 31.5 | 31 | 29.8 | 27.4 | 35.7 | 32.5 |
| Antibacterial activity (%) | 50.7 | 49.8 | 38.7 | 50.5 | 51.5 | 52.7 | 50.5 | 53.5 |
| Skin irritation (grade) | 2 | 2 | 2 | 2 | 2 | 2 | 1 | 1 |
| Abrasion resistance (cycles) | 15,800 | 14,700 | 10,170 | 20,000 or more | 20,000 or more | 20,000 or more | 8,000 | 17000 |
| Contact cooling sensation (W/cm²) | 0.188 | 0.178 | 0.201 | 0.195 | 0.182 | 0.180 | 0.163 | 0.186 |
| Thermal conductivity in the thickness direction at 20° C. (W/mK) | 0.0858 | 0.0823 | 0.0801 | 0.9204 | 0.0858 | 0.0721 | 0.0750 | 0.0882 |
| Washing durability — Peeling resistance (grade) | 2 | 2 | 2 | 2 | 3 | 3 | 2 | 3 |
| Heat retention rate (%) | 22.1 | 22.7 | 26.9 | 32 | 35.7 | 40.1 | 34.2 | 30.3 |
| Skin irritation (grade) | 2 | 2 | 2 | 2 | 2 | 3 | 1 | 2 |
| Antibacterial activity (%) | 48.4 | 41.2 | 30.5 | 50.1 | 47.1 | 40.1 | 50.5 | 51.3 |

Referring to Tables 3 and 4, it was confirmed that the functional fabric according to the present invention had both an excellent cool feeling and very low skin irritation. In addition, it could be confirmed that in the case of the functional fabric according to the present invention, since the durability was excellent, the pilling to be generated was small, and the abrasion resistance was significantly excellent, the nap was not generated even after being washed, the damage of the fabric was small even after being washed, and the functionality was continuously maintained. Furthermore, it was confirmed that the functional fabric according to the present invention had a high antibacterial property.

Hereinabove, although the present invention has been described by specific matters, exemplary embodiments, and drawings, they have been provided only for assisting in the entire understanding of the present invention. Therefore, the present invention is not limited to the exemplary embodiments. Various modifications and changes may be made by those skilled in the art to which the present invention pertains from this description.

Therefore, the spirit of the present invention should not be limited to the above-described exemplary embodiments, and the following claims as well as all modified equally or equivalently to the claims are intended to fall within the scope and spirit of the invention.

The invention claimed is:

1. A functional fabric comprising a knitted fabric using a polyethylene yarn which has a melt index (MI) of 0.1 to 5 g/10 min as measured in accordance with ASTM D1238, a polydispersity index of more than 5 and 12 or less, and a degree of crystallinity of 60 to 90%, wherein the fabric has a surface density of 100 to 800 g/m² and a peeling resistance of grade 4 or higher as measured at a number of revolutions of 14,400 in accordance with a peeling box method specified in KS K ISO 12945-1:2014, wherein the polyethylene yarn has an initial modulus in accordance with ASTM D2256 of 100 to 300 g/d and an elongation of 6 to 12%.

2. The functional fabric of claim 1, wherein the fabric has a heat retention rate in accordance with KS K 0560:2018, method B of 30% or less.

3. The functional fabric of claim 1, wherein the fabric has an antibacterial activity in accordance with KS K 0693:2016 of 50% or more and an ammonia deodorization rate of 10 to 30% as measured for 30 minutes to 120 minutes by a gas detection tube method.

4. The functional fabric of claim 1, wherein the fabric has an abrasion resistance of 20,000 cycles or more as measured in accordance with a Martindale method specified in KS K ISO 12947-2:2014.

5. The functional fabric of claim 1, wherein the fabric has a contact cooling sensation of 0.2 $W/cm^2$ or more as measured at 20±2° C. and 65±2% R.H and a thermal conductivity in the thickness direction at 20° C. of 0.1 W/mK or more.

6. The functional fabric of claim 1, wherein the polyethylene yarn has a density of 0.941 to 0.965 $g/cm^3$ and a weight average molecular weight of 90,000 to 400,000 g/mol.

7. The functional fabric of claim 1, wherein the polyethylene yarn has a tensile strength of 10 to 20 g/d.

8. The functional fabric of claim 1, wherein the polyethylene yarn has a circular cross section.

9. The functional fabric of claim 1, wherein the polyethylene yarn includes 25 to 500 filaments, each having a fineness of 1 to 3 denier, and has a total fineness of 50 to 500 denier.

10. The functional fabric of claim 1, wherein the fabric has a water contact angle of 110° or more.

11. The functional fabric of claim 1, wherein the fabric has a peeling resistance of grade 4 or higher, as measured at a number of revolutions of 14,400 in accordance with a peeling box method specified in KS K ISO 12945-1:2014, after performing a washing and drying process 100 times in a washing machine standard course.

12. A cooling mask comprising the functional fabric of claim 1.

* * * * *